(12) United States Patent  (10) Patent No.: US 12,296,201 B2
Inaba et al.  (45) Date of Patent: May 13, 2025

(54) TREATMENT SYSTEM, CONTROL DEVICE, AND CONTROL METHOD

(71) Applicant: OLYMPUS CORPORATION, Hachioji (JP)

(72) Inventors: Kizuku Inaba, Hirosaki (JP); Ryu Onuma, Tama (JP); Satoshi Honda, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 812 days.

(21) Appl. No.: 17/523,423

(22) Filed: Nov. 10, 2021

(65) Prior Publication Data

US 2022/0062662 A1  Mar. 3, 2022

Related U.S. Application Data

(63) Continuation of application No. PCT/JP2019/038683, filed on Oct. 1, 2019.

(51) Int. Cl.
*A61B 18/14* (2006.01)
*A61N 7/00* (2006.01)
*A61B 18/00* (2006.01)

(52) U.S. Cl.
CPC ............... *A61N 7/00* (2013.01); *A61B 18/14* (2013.01); *A61B 2018/00845* (2013.01);
(Continued)

(58) Field of Classification Search
CPC .. A61B 17/320068; A61B 2017/00022; A61B 2017/0003; A61B 2017/00137; A61B 2017/00367; A61B 18/1206; A61B 18/14; A61B 2018/00827; A61B 2018/00845; A61B 2018/00869; A61B 2018/00875; A61B 2018/00892; A61B 2018/00898; A61B 2018/00994;
(Continued)

(56) References Cited

U.S. PATENT DOCUMENTS 6,383,183 B1 * 5/2002 Sekino ............... A61B 18/1206
606/49
2015/0142031 A1  5/2015 Faller et al.
(Continued)

FOREIGN PATENT DOCUMENTS

DE 102015225345 A1 6/2017
JP 2009-254818 A 11/2009
(Continued)

OTHER PUBLICATIONS

Dec. 10, 2019 International Search Report issued in International Patent Application No. PCT/JP2019/038683.

*Primary Examiner* — Khadijeh A Vahdat
(74) *Attorney, Agent, or Firm* — Oliff PLC

(57) ABSTRACT

A treatment system can include a treatment tool including an ultrasound transducer and an end effector. The system can also include an ultrasound power source configured to output a drive signal to the ultrasound transducer, and a processor configured to detect an abnormality in the end effector, and whether end effector is immersed in a liquid. The system can continue an output of the drive signal from the ultrasound power source to the ultrasound transducer when the abnormality is detected and the end effector is immersed in the liquid.

20 Claims, 12 Drawing Sheets

(52) U.S. Cl.
CPC ............... *A61B 2018/00875* (2013.01); *A61B 2018/00892* (2013.01); *A61B 2018/00994* (2013.01)

(58) Field of Classification Search
CPC .... A61B 2018/1253; A61B 2018/1273; A61B 2018/128; A61B 2090/0809
See application file for complete search history.

(56) References Cited

U.S. PATENT DOCUMENTS

2017/0202604 A1    7/2017  Tanigami et al.
2019/0274752 A1*  9/2019  Denzinger ..... A61B 17/320068

FOREIGN PATENT DOCUMENTS

| | | |
|---|---|---|
| JP | 2016-537098 A | 12/2016 |
| WO | 2017/018171 A1 | 2/2017 |

* cited by examiner

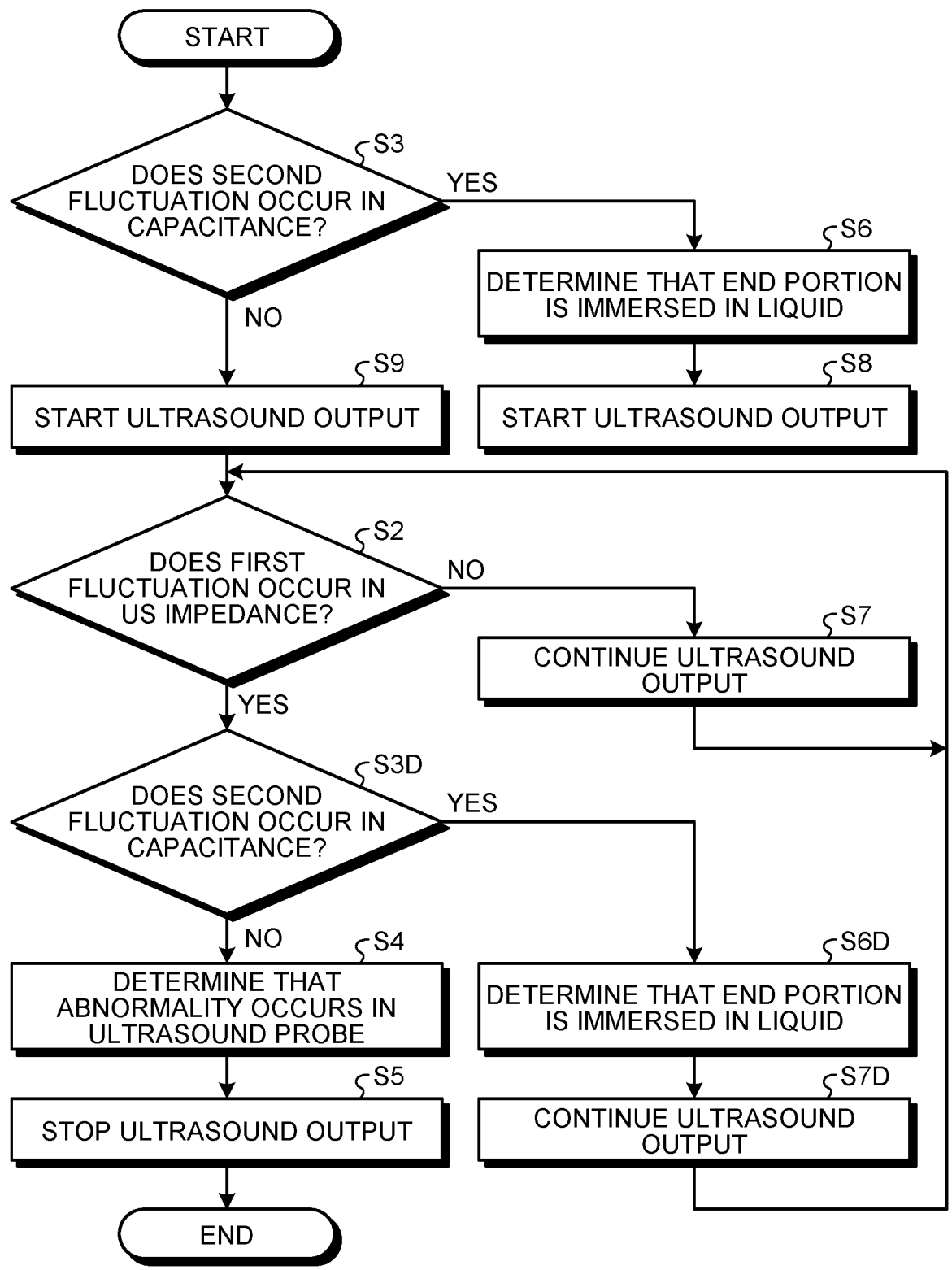

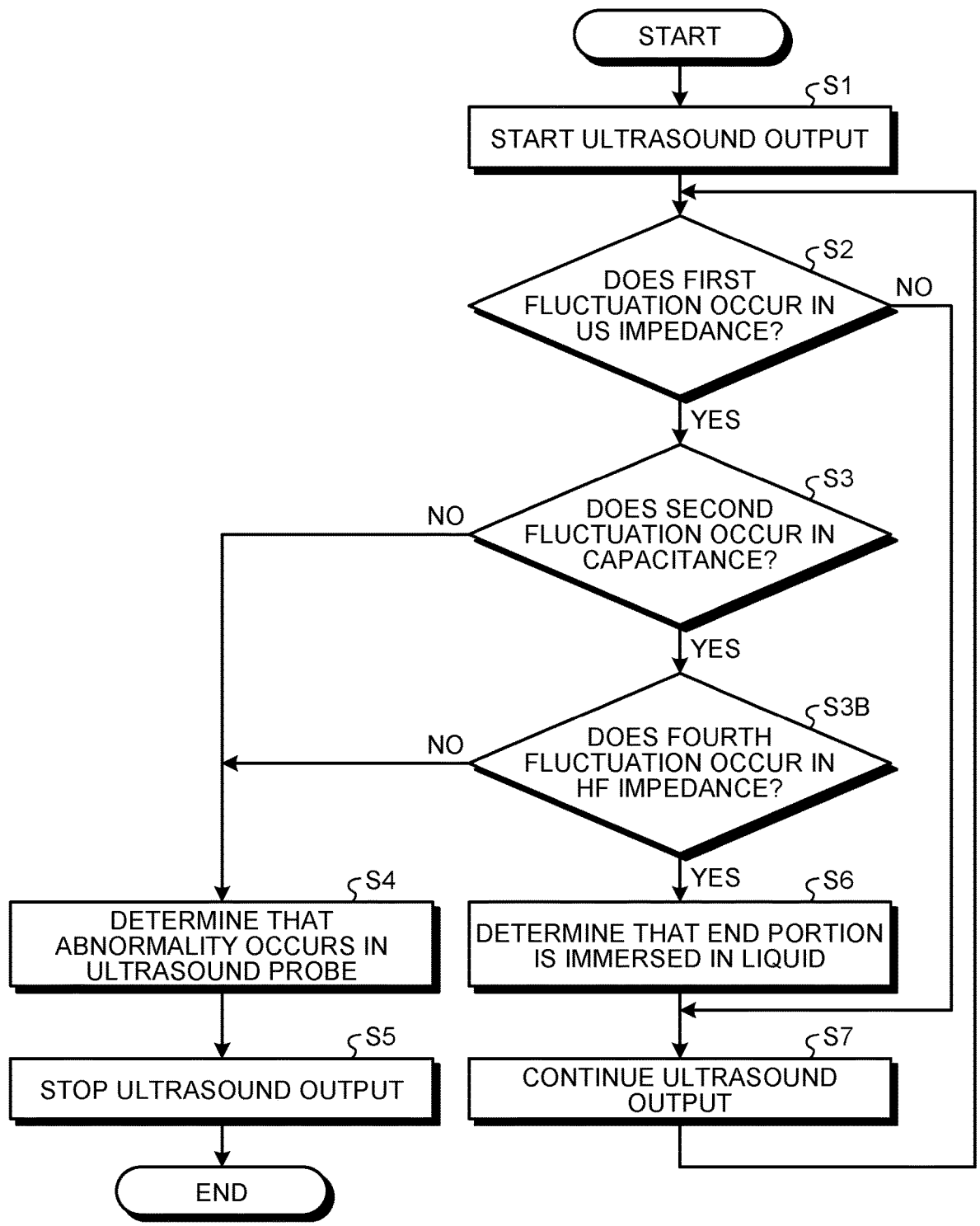

TREATMENT SYSTEM, CONTROL DEVICE, AND CONTROL METHOD

CROSS-REFERENCE TO RELATED APPLICATION

This application is a continuation of International Application No. PCT/JP2019/038683, filed on Oct. 1, 2019, the entire contents of which are incorporated herein by reference.

BACKGROUND

1. Technical Field

The present disclosure relates to a treatment system, a control device, and a control method.

2. Related Art

In the related art, a treatment system that treats a living tissue by applying ultrasound energy to the living tissue is known (for example, see JP 2009-254818 A).

The treatment system described in JP 2009-254818 A includes an ultrasound treatment tool and a control device, which will be described below.

The ultrasound treatment tool includes an ultrasound transducer that generates ultrasound vibration in accordance with a supplied drive signal, and an end effector that applies the ultrasound vibration to the living tissue (applies ultrasound energy to the living tissue).

The control device includes an ultrasound power source that outputs a drive signal to the ultrasound transducer.

Here, the control device determines whether or not an abnormality (for example, a crack or the like) occurs in the end effector on the basis of a fluctuation in an impedance value (hereinafter, referred to as US impedance) on the basis of a voltage value and a current value in the drive signal output from the ultrasound power source. Hereinafter, supplying the drive signal to the ultrasound transducer to subject the end effector to ultrasound vibration is referred to as an ultrasound output. Then, in a case where it is determined that the abnormality has occurred in the end effector during the ultrasound output, the control device stops the ultrasound output.

SUMMARY

In exemplary embodiments, a treatment system can include a treatment tool including an ultrasound transducer configured to generate ultrasound vibration in accordance with a supplied drive signal, and an end effector configured to apply the ultrasound vibration to a living tissue to treat the living tissue. The system can also include an ultrasound power source configured to output the drive signal to the ultrasound transducer, and a processor configured to control an operation of the ultrasound power source. The processor can detect whether or not an abnormality occurs in the end effector, determine whether or not the end effector is immersed in a liquid, and continue an output of the drive signal from the ultrasound power source to the ultrasound transducer when there is an abnormality in the end effector and the end effector is immersed in the liquid.

In exemplary embodiments, a control device can include an ultrasound power source that is connected to a treatment tool including an ultrasound transducer configured to generate ultrasound vibration in accordance with a supplied drive signal and an end effector configured to apply the ultrasound vibration to a living tissue to treats the living tissue, the ultrasound power source being configured to output the drive signal to the ultrasound transducer; and a processor configured to control an operation of the ultrasound power source, the processor being configured to determine whether or not an abnormality occurs in the end effector, determine whether or not the end effector is immersed in a liquid, and continue an output of the drive signal from the ultrasound power source to the ultrasound transducer in a case where it is determined that the abnormality occurs in the end effector and that the end effector is immersed in the liquid when the ultrasound power source outputs the drive signal to the ultrasound transducer.

In exemplary embodiments, provided is a control method executed by a processor of a treatment system. The method includes: determining whether or not an abnormality occurs in an end effector configured to apply ultrasound vibration to a living tissue to treat the living tissue, the ultrasound vibration being generated by an ultrasound transducer in accordance with a drive signal supplied from an ultrasound power source; determining whether or not the end effector is immersed in a liquid; and continuing an output of the drive signal from the ultrasound power source to the ultrasound transducer in a case where it is determined that the abnormality occurs in the end effector and that the end effector is immersed in the liquid when the ultrasound power source outputs the drive signal to the ultrasound transducer.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 11 is a flowchart illustrating another exemplary embodiment; and

FIG. 12 is a flowchart illustrating another exemplary embodiment.

DETAILED DESCRIPTION

Figure 1:
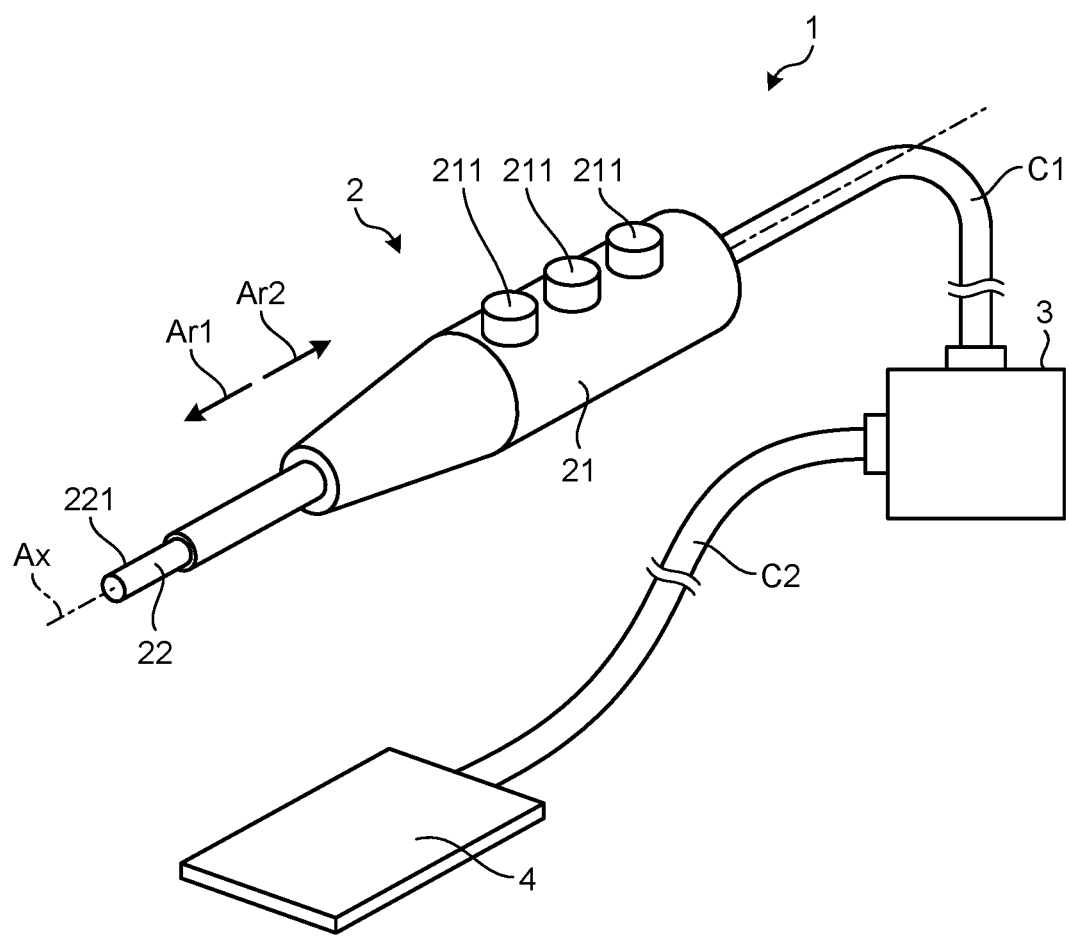
FIG. 1 is a view illustrating a treatment system according to an exemplary embodiment.

Hereinafter, modes for carrying out the disclosure (hereinafter, embodiments) will be described with reference to the drawings. The disclosure is not limited by the embodiments to be described below. Furthermore, in illustration of the drawings, the same portions are denoted by the same reference numerals.

First Embodiment

Schematic Configuration of Treatment System

Figure 2:
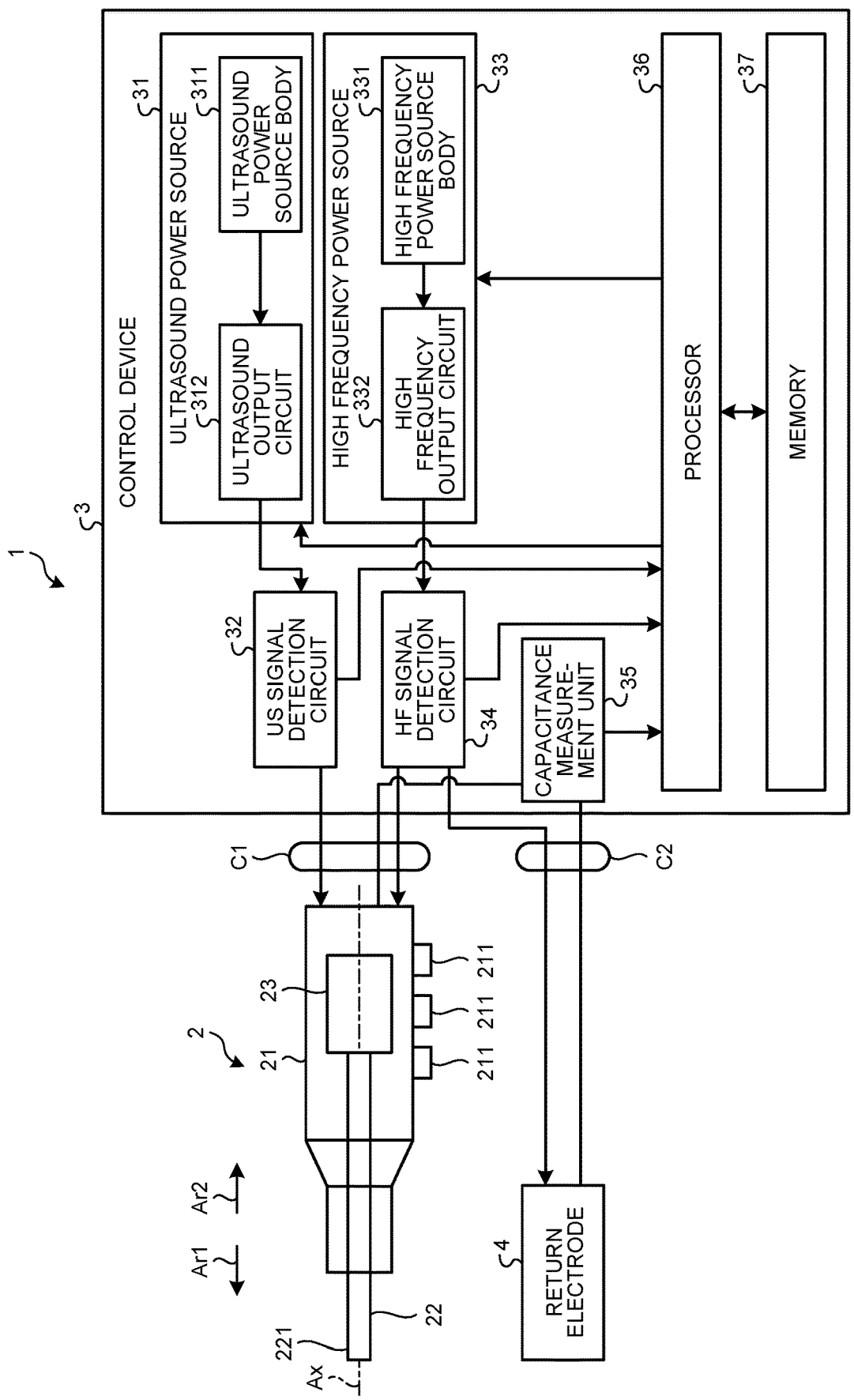
FIG. 2 is a diagram illustrating an internal configuration of a treatment tool and a control device.

FIG. 1 is a view illustrating a treatment system 1 according to a first embodiment. FIG. 2 is a diagram illustrating an internal configuration of a treatment tool 2 and a control device 3.

The treatment system 1 applies ultrasound energy and high frequency energy to a treatment target site (hereinafter, referred to as a target site) in a living tissue to treat the target site. Examples of the treatment that can be performed by the treatment system 1 according to the first embodiment include coagulation and incision of the target site. As illustrated in FIG. 1 or 2, the treatment system 1 includes the treatment tool 2, the control device 3, and a return electrode 4 attached to a surface of a subject.

Configurations of the treatment tool 2 and the control device 3 will be described below.

Configuration of Treatment Tool

As illustrated in FIG. 1 or 2, the treatment tool 2 includes a housing 21, an ultrasound probe 22, and an ultrasound transducer 23.

Hereinafter, as illustrated in FIG. 1 or 2, one side along a central axis Ax of the ultrasound probe 22 is referred to as a distal end side Ar1, and the other side is referred to as a proximal end side Ar2.

The housing 21 has a substantially cylindrical shape extending along the central axis Ax and supports the ultrasound probe 22 and the ultrasound transducer 23.

As illustrated in FIG. 1 or 2, the housing 21 is provided with switches 211 that are exposed to the outside and receive a treatment start operation and a treatment end operation from an operator, respectively. Then, the switches 211 output an operation signal corresponding to the treatment start operation and an operation signal corresponding to the treatment end operation to the control device 3, respectively via a first electric cable C1 (FIGS. 1 and 2) that electrically connects the treatment tool 2 to the control device 3.

The ultrasound probe 22 corresponds to an end effector. The ultrasound probe 22 has an elongated shape extending along the central axis Ax and is made of an electric conductive material. The ultrasound probe 22 is attached inside the housing 21 in a state in which an end portion 221 (FIGS. 1 and 2) on the distal end side Ar1 is exposed to the outside. Furthermore, the ultrasound probe 22 has an end portion on the proximal end side Ar2 connected to a bolted Langevin-type transducer (BLT) configuring the ultrasound transducer 23. Then, the ultrasound probe 22 transmits the ultrasound vibration generated by the BLT from the end portion on the proximal end side Ar2 to the end portion 221 on the distal end side Ar1.

The ultrasound transducer 23 is inserted into the housing 21 from the proximal end side Ar2 of the housing 21 and is configured to be attachable to and detachable from the housing 21. The ultrasound transducer 23 includes the above-described BLT (not illustrated) and generates the ultrasound vibration in accordance with supply of a drive signal that is AC power. That is, the ultrasound transducer 23 corresponds to the ultrasound transducer.

Configuration of Control Device

The treatment tool 2 is detachably connected to the control device 3 by the first electric cable C1. The return electrode 4 is detachably connected to the control device 3 by a second electric cable C2 (FIGS. 1, and 2). As illustrated in FIG. 2, the control device 3 includes an ultrasound power source 31, a US signal detection circuit 32, a high frequency power source 33, an HF signal detection circuit 34, a capacitance measurement unit 35, a processor 36, and a memory 37.

The ultrasound power source 31 outputs a drive signal to the ultrasound transducer 23 via the first electric cable C1 under control of the processor 36. As illustrated in FIG. 2, the ultrasound power source 31 includes an ultrasound power source body 311 and an ultrasound output circuit 312.

The ultrasound power source body 311 is a main power source in the ultrasound power source 31.

Under the control of the processor 36, the ultrasound output circuit 312 converts (boosts or the like) power output from the ultrasound power source body 311, and outputs the drive signal to the ultrasound transducer 23 via the first electric cable C1. Then, the ultrasound transducer 23 generates the ultrasound vibration in accordance with the drive signal to subject the ultrasound probe 22 to the ultrasound vibration. The ultrasound vibration is applied to a target site in contact with the ultrasound probe 22 from the ultrasound probe 22. In other words, the ultrasound energy is applied to the target site.

Hereinafter, supplying the drive signal to the ultrasound transducer 23 to subject the ultrasound probe 22 to the ultrasound vibration is referred to as an ultrasound output.

The US signal detection circuit 32 detects a US signal on the basis of the drive signal output from the ultrasound power source 31 (ultrasound output circuit 312) to the ultrasound transducer 23. Then, the US signal detection circuit 32 outputs the detected US signal to the processor 36.

Here, examples of the US signal include a phase signal of a voltage in the drive signal (hereinafter, referred to as a US voltage phase signal), a phase signal of a current in the drive signal (hereinafter, referred to as a US current phase signal), a current value in the drive signal (hereinafter, referred to as a US current), a voltage value in the drive signal (hereinafter, referred to as a US voltage), an impedance value calculated from the US current and the US voltage (hereinafter, referred to as a US impedance), and the like.

The high frequency power source 33 outputs a high frequency signal, which is high frequency power, between the ultrasound probe 22 and the return electrode 4 via the first and second electric cables C1 and C2 under the control of the processor 36. As illustrated in FIG. 2, the high frequency power source 33 includes a high frequency power source body 331 and a high frequency output circuit 332.

The high frequency power source body 331 is a main power source in the high frequency power source 33.

Under the control of the processor 36, the high frequency output circuit 332 converts (boosts or the like) power output from the high frequency power source body 331, and outputs a high frequency signal between the ultrasound probe 22 and the return electrode 4 via the first and second electric cables C1 and C2. A high frequency current flows through the target site positioned between the ultrasound probe 22 and the return electrode 4. In other words, the high frequency energy is applied to the target site.

The HF signal detection circuit 34 detects an HF signal on the basis of the high frequency signal output between the ultrasound probe 22 and the return electrode 4 from the high frequency power source 33 (high frequency output circuit 332). Then, the HF signal detection circuit 34 outputs the detected HF signal to the processor 36.

Here, examples of the HF signal include a phase signal of a voltage in the high frequency signal (hereinafter, referred to as an HF voltage phase signal), a phase signal of a current in the high frequency signal (hereinafter, referred to as an HF current phase signal), a current value in the high frequency signal (hereinafter, referred to as an HF current), a voltage value in the high frequency signal (hereinafter, referred to as an HF voltage), an impedance value calculated from the HF current and the HF voltage (hereinafter, referred to as an HF impedance Z), and the like. The HF impedance Z corresponds to a high frequency impedance.

The capacitance measurement unit 35 measures capacitance between the treatment tool 2 (end portion 221) and a ground. Examples of the capacitance measurement unit 35 include an LCR meter, and the like having the ultrasound probe 22 and the return electrode 4 as a terminal via the first and second electric cables C1 and C2. Then, the capacitance measurement unit 35 outputs a signal corresponding to the measured capacitance to the processor 36.

The processor 36 is, for example, a central processing unit (CPU), a field-programmable gate array (FPGA), or the like, and controls the entire operation of the treatment system 1 according to a program stored in the memory 37.

A function of the processor 36 will be described in "Control Method" to be described later.

The memory 37 stores a program executed by the processor 36, information necessary for processing of the processor 36, and the like.

Control Method

Next, the control method executed by the processor 36 will be described.

Figure 3:
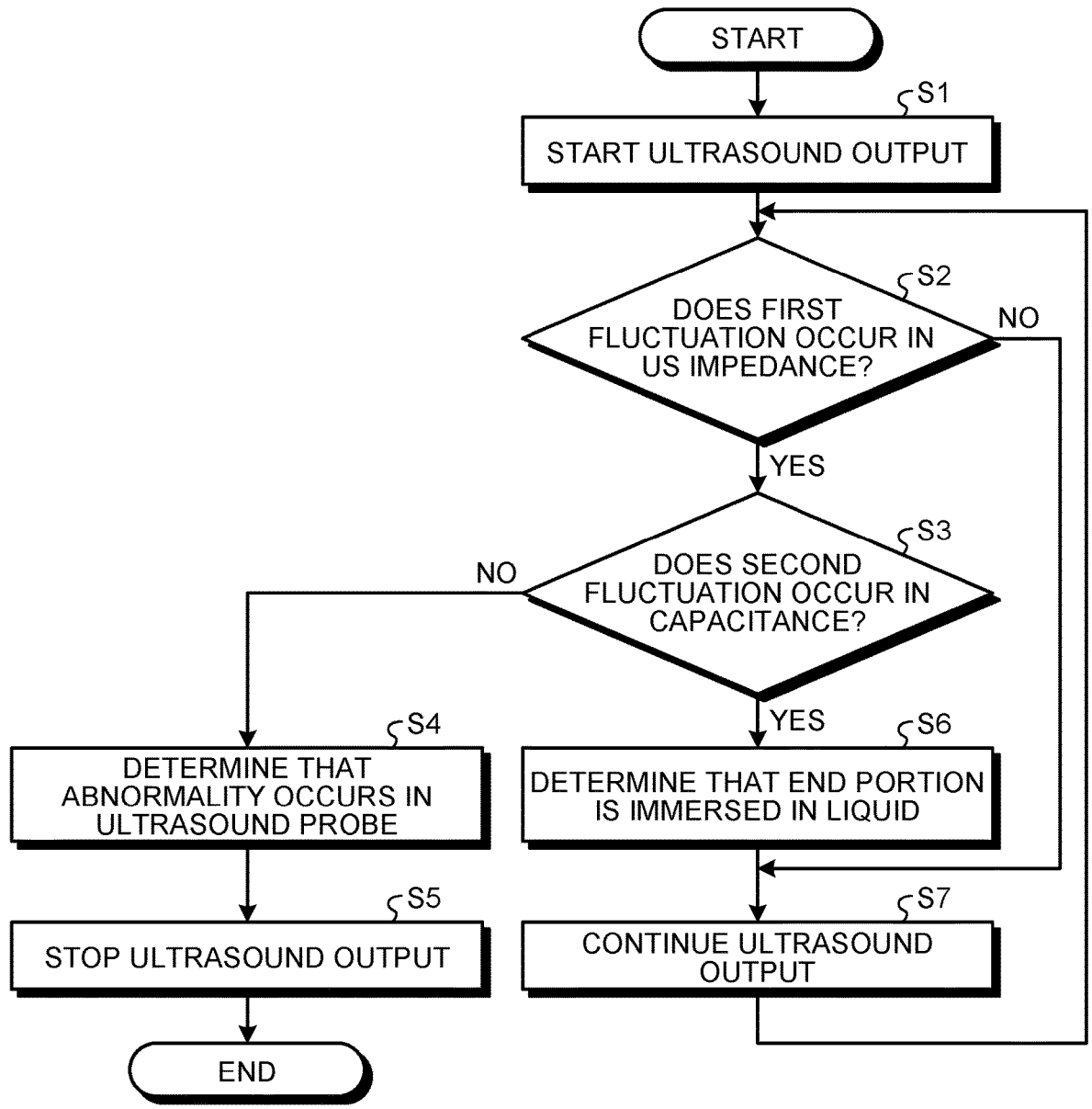
FIG. 3 is a flowchart illustrating a control method.
Figure 4:
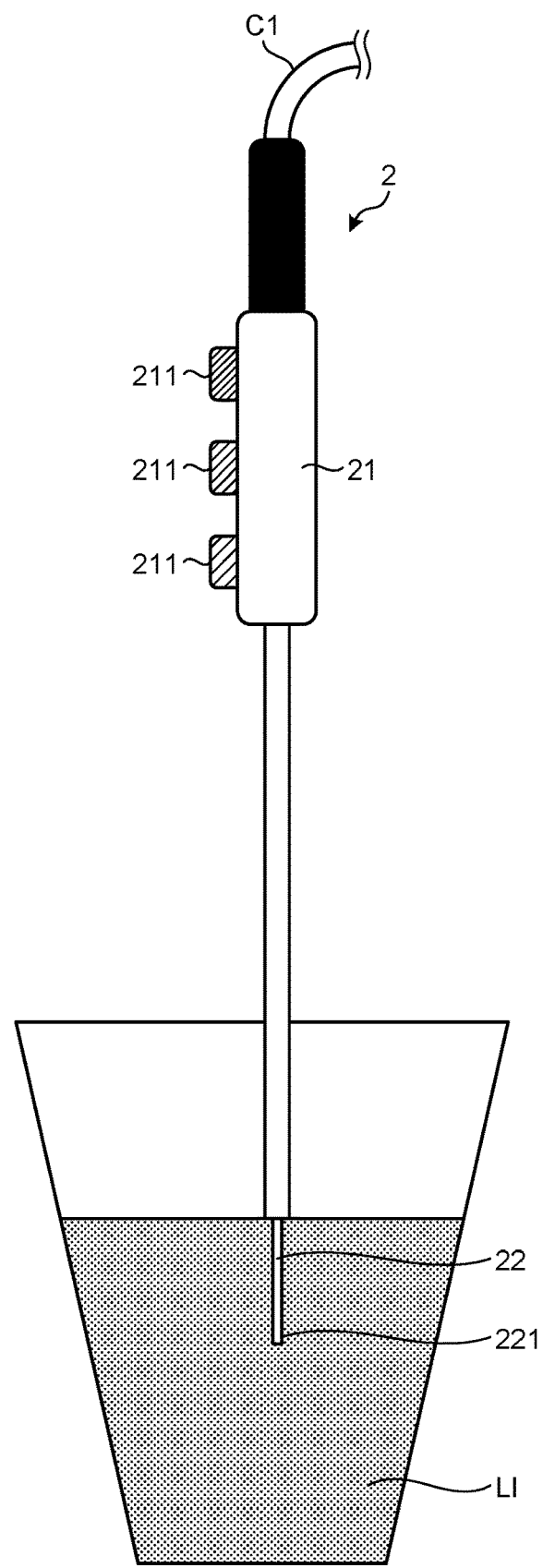
FIG. 4 is a diagram for describing the control method illustrated in FIG. 3.
Figure 5:
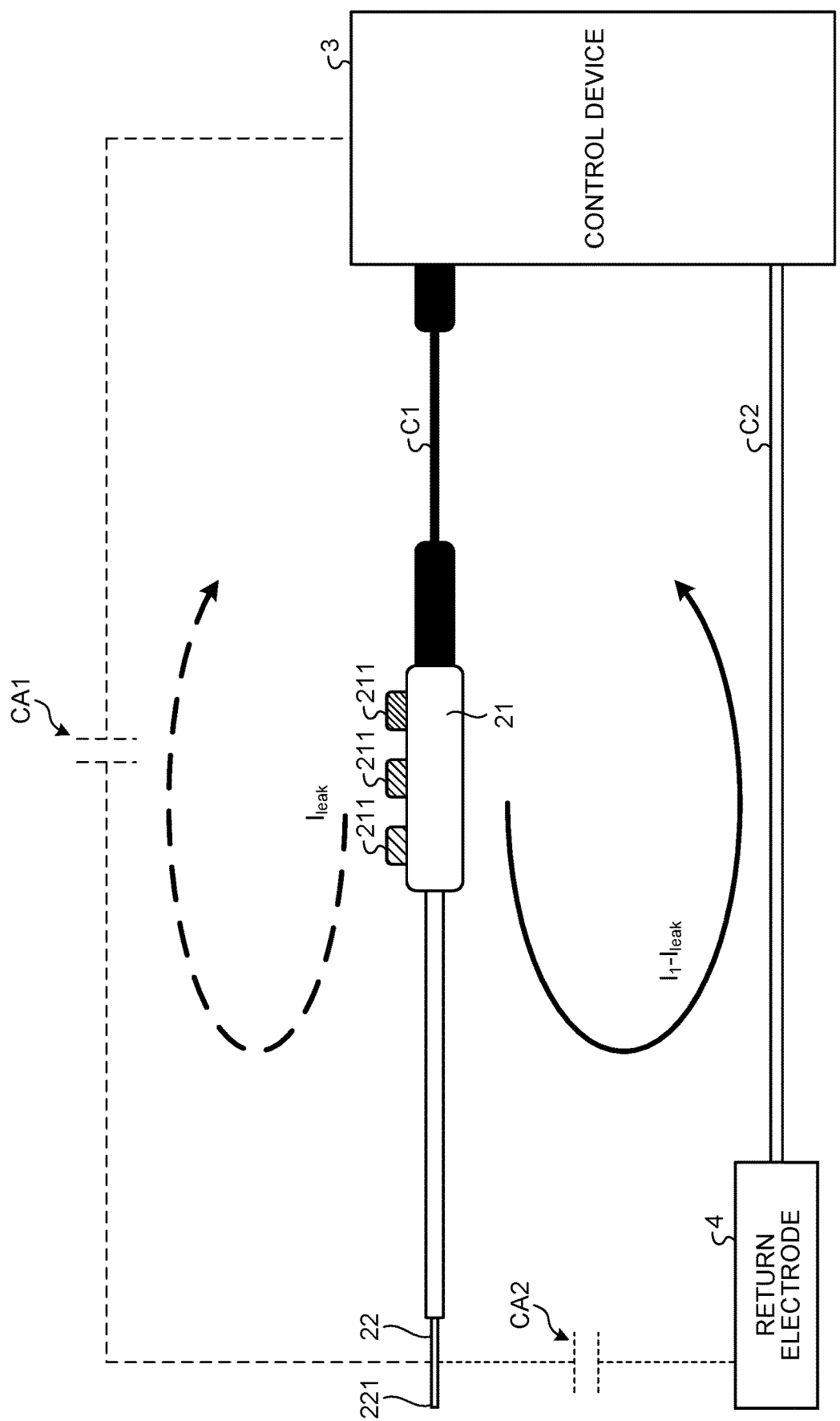
FIG. 5 is a diagram for describing the control method illustrated in FIG. 3.

FIG. 3 is a flowchart illustrating the control method. FIGS. 4 and 5 are diagrams for describing the control method illustrated in FIG. 3. Specifically, FIG. 4 is a diagram illustrating a method of cleaning the treatment tool 2. FIG. 5 is a diagram schematically illustrating capacitance measured by the capacitance measurement unit 35.

The control method is an effective control method for performing the cleaning method illustrated in FIG. 4. Specifically, as illustrated in FIG. 4, the cleaning method is a cleaning method in which the ultrasound output is performed in a state in which the end portion 221 of the ultrasound probe 22 is immersed in a liquid LI such as water, and foreign matter adhering to the end portion 221 is removed by the ultrasound vibration of the ultrasound probe 22.

First, the processor 36 controls the operation of the ultrasound power source 31 according to the treatment start operation on the switches 211 by a user, and starts the ultrasound output (Step S1).

After Step S1, the processor 36 monitors the US signal (US impedance) output from the US signal detection circuit 32, and determines whether or not a first fluctuation occurs in the US impedance (Step S2). Here, in Step S2, the processor 36 determines whether or not there is a possibility that an abnormality has occurred in the ultrasound probe 22 by determining whether or not the first fluctuation occurs in the US impedance.

In a case where it is determined that the first fluctuation does not occur in the US impedance (Step S2: No), the processor 36 causes the processing to proceed to Step S7.

On the other hand, in a case where it is determined that the first fluctuation occurs in the US impedance (Step S2: Yes), the processor 36 monitors the signal output from the capacitance measurement unit 35 (capacitance CA1 (FIG. 5) between the treatment tool 2 (end portion 221) and the ground), and determines whether or not a second fluctuation occurs in the capacitance CA1 (Step S3).

Meanwhile, when the target site is treated, since a living tissue CA2 (FIG. 5) is located between the end portion 221 and the return electrode 4, the HF circuit that applies the high frequency energy to the target site is in a closed state using the return electrode 4, which follows a path of the control device 3, the first electric cable C1, the treatment tool 2 (end portion 221), the living tissue CA2, the return electrode 4, the second electric cable C2, and the control device 3.

On the other hand, when the cleaning method illustrated in FIG. 4 is performed, the HF circuit is in an open state without using the return electrode 4, which follows a path of the control device 3, the first electric cable C1, the treatment tool 2 (end portion 221), the liquid LI, and the ground. In the open state, the capacitance CA1 between the treatment tool 2 (end portion 221) and the ground is increased by the capacitance of the liquid LI as compared with the closed state or the state immediately before the end portion 221 is immersed in the liquid LI.

That is, even in a case where the first fluctuation occurs in the US impedance (Step S2: Yes), when the second fluctuation occurs in the capacitance CA1 (Step S3: Yes), it can be determined that the first fluctuation in the US impedance is not caused by the occurrence of the abnormality (for example, a crack or the like) in the ultrasound probe 22, but is caused by the immersion of the end portion 221 in the liquid LI (caused by the resistance of the liquid LI to the ultrasound vibration). On the other hand, in a case where the first fluctuation occurs in the US impedance (Step S2: Yes) and the second fluctuation does not occur in the capacitance CA1 (Step S3: No), it can be determined that the first fluctuation in the US impedance is caused by the occurrence of the abnormality in the ultrasound probe 22.

Then, in a case where it is determined that the second fluctuation does not occur in the capacitance CA1 (Step S3: No), the processor 36 determines that the abnormality has occurred in the ultrasound probe 22 (Step S4), and stops the operation of the ultrasound power source 31 (stops the ultrasound output) (Step S5). After that, the processor 36 ends this control flow.

On the other hand, in a case where it is determined that the second fluctuation occurs in the capacitance CA1 (Step S3: Yes), the processor 36 determines that the end portion 221 is immersed in the liquid LI (Step S6), and continues the ultrasound output (Step S7). After that, the processor 36 causes the processing to return to Step S2. While Steps S2, S3, S6, and S7 are executed repeatedly, in a case where the treatment end operation is performed on the switches 211 by the user, the processor 36 stops the operation of the ultrasound power source 31 (stops the ultrasound output).

According to the first embodiment described above, the following effects are obtained.

In a case where the processor 36 according to the first embodiment determines that the end portion 221 is immersed in the liquid after starting the ultrasound output, the processor 36 continues the ultrasound output even when it is determined that the abnormality occurs in the ultrasound probe 22.

Therefore, according to the first embodiment, even in a case where the cleaning method illustrated in FIG. 4 is performed, the ultrasound output is not stopped due to erroneous determination that the abnormality occurs in the ultrasound probe 22, and convenience can be improved.

Second Embodiment

Next, the second embodiment will be described.

In the following description, the same reference numerals are given to the same configurations as those of the above-described first embodiment, and the detailed description thereof will be omitted or simplified.

Figure 6:
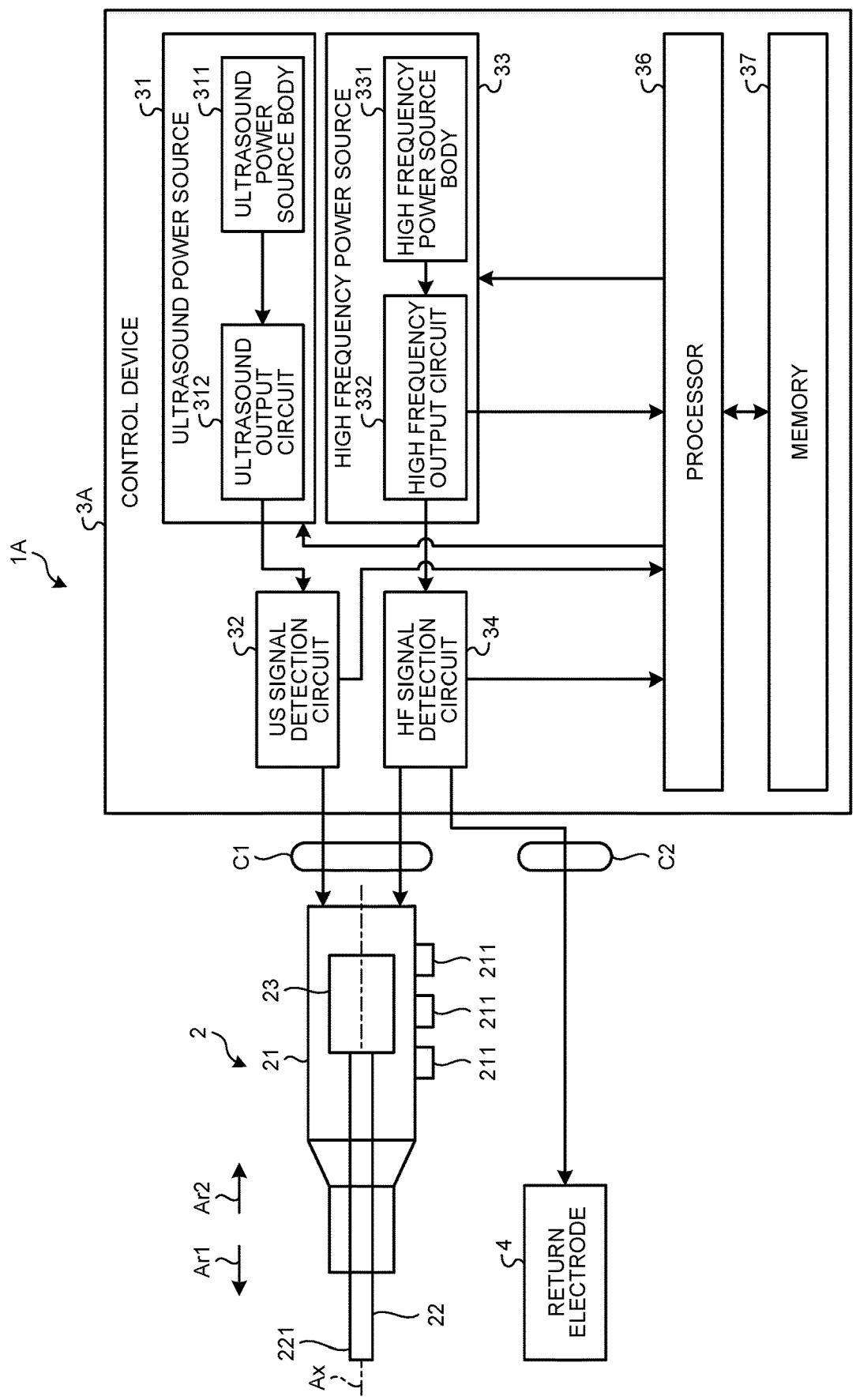
FIG. 6 is a diagram illustrating a configuration of a control device according to another exemplary embodiment.
Figure 7:
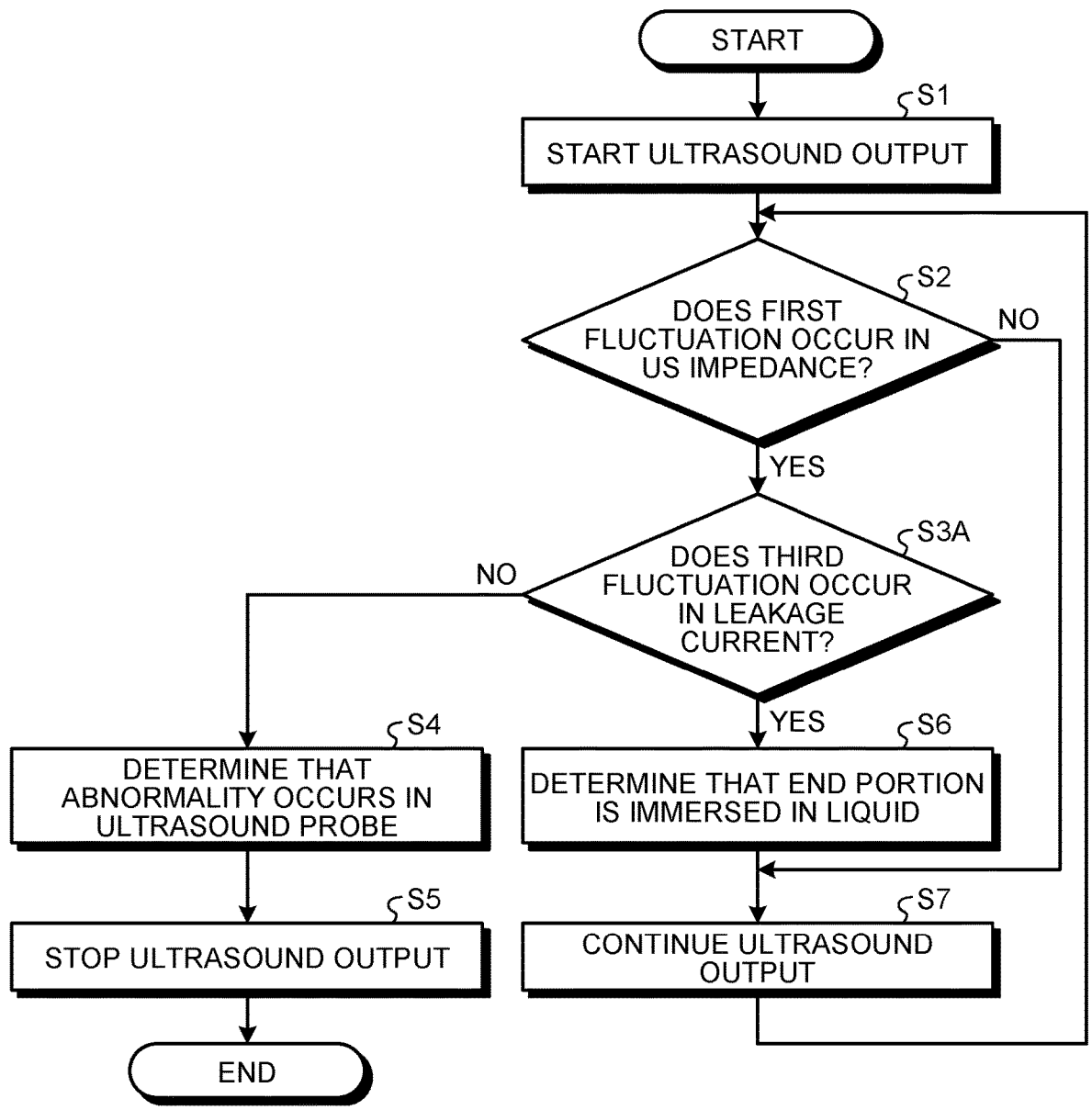
FIG. 7 is a flowchart illustrating a control method according to the exemplary embodiment shown in FIG. 6.

FIG. 6 is a diagram illustrating a configuration of a control device 3A according to the second embodiment. FIG. 7 is a flowchart illustrating a control method according to the second embodiment.

In the above-described first embodiment, the processor 36 determines whether or not the end portion 221 is immersed in the liquid LI (whether or not the cleaning method illustrated in FIG. 4 is being performed) on the basis of the fluctuation in the capacitance CA1.

On the other hand, in the second embodiment, the processor 36 determines whether or not the end portion 221 is immersed in the liquid LI on the basis of the fluctuation in a leakage current between the end portion 221 and the ground. That is, in a treatment system 1A (control device 3A) according to the second embodiment, as illustrated in FIG. 6, the capacitance measurement unit 35 of the treatment system 1 (control device 3) described in the first embodiment described above is omitted.

Hereinafter, the control method according to the second embodiment will be described.

In the control method according to the second embodiment, as illustrated in FIG. 7, Step S3A is adopted instead of Step S3 in the control method described in the first embodiment described above. Therefore, only Step S3A will be described below.

Step S3A is executed in a case where it is determined that the first fluctuation occurs in the US impedance (Step S2: Yes).

Specifically, in Step S3A, the processor 36 calculates a leakage current $I_{leak}$ (FIG. 5) between the treatment tool 2 (end portion 221) and the ground as will be described below.

The processor 36 acquires, from the high frequency output circuit 332, a current value $I_1$ of the high frequency signal that is output between the ultrasound probe 22 and the return electrode 4 by the high frequency output circuit 332. The processor 36 acquires, from the HF signal detection circuit 34, a current value $(I_1-I_{leak})$ actually flowing between the ultrasound probe 22 and the return electrode 4. The current value $(I_1-I_{leak})$ corresponds to the HF current. The processor 36 calculates the leakage current $I_{leak}$ from the current value $I_1$ and the current value $(I_1-I_{leak})$.

Then, the processor 36 monitors the leakage current $I_{leak}$ and determines whether or not a third fluctuation occurs in the leakage current $I_{leak}$.

Meanwhile, as described above, in a case where the HF circuit is in the open state, the capacitance CA1 is increased due to the capacitance of the liquid LI as compared with the closed state or the state immediately before the end portion 221 is immersed in the liquid LI. As a result, the leakage current $I_{leak}$ is also increased.

That is, even in a case where the first fluctuation occurs in the US impedance (Step S2: Yes), when the third fluctuation occurs in the leakage current $I_{leak}$ (Step S3A: Yes), it can be determined that the first fluctuation in the US impedance is not caused by the occurrence of the abnormality (for example, a crack or the like) in the ultrasound probe 22, but is caused by the immersion of the end portion 221 in the liquid LI. On the other hand, in a case where the first fluctuation occurs in the US impedance (Step S2: Yes) and the third fluctuation does not occur in the leakage current $I_{leak}$ (Step S3A: No), it can be determined that the first fluctuation in the US impedance is caused by the occurrence of the abnormality in the ultrasound probe 22.

In a case where it is determined that the third fluctuation does not occur in the leakage current $I_{leak}$ (Step S3A: No), the processor 36 causes the processing to proceed to Step S4. On the other hand, in a case where it is determined that the third fluctuation occurs in the leakage current $I_{leak}$ (Step S3A: Yes), the processor 36 causes the processing to proceed to Step S6.

Even in a case where it is determined whether or not the end portion 221 is immersed in the liquid LI on the basis of the fluctuation in the leakage current $I_{leak}$ as in the second embodiment described above, the same effects as those of the first embodiment described above are obtained.

Third Embodiment

Next, the third embodiment will be described.

In the following description, the same reference numerals are given to the same configurations as those of the above-described first embodiment, and the detailed description thereof will be omitted or simplified.

Figure 8:
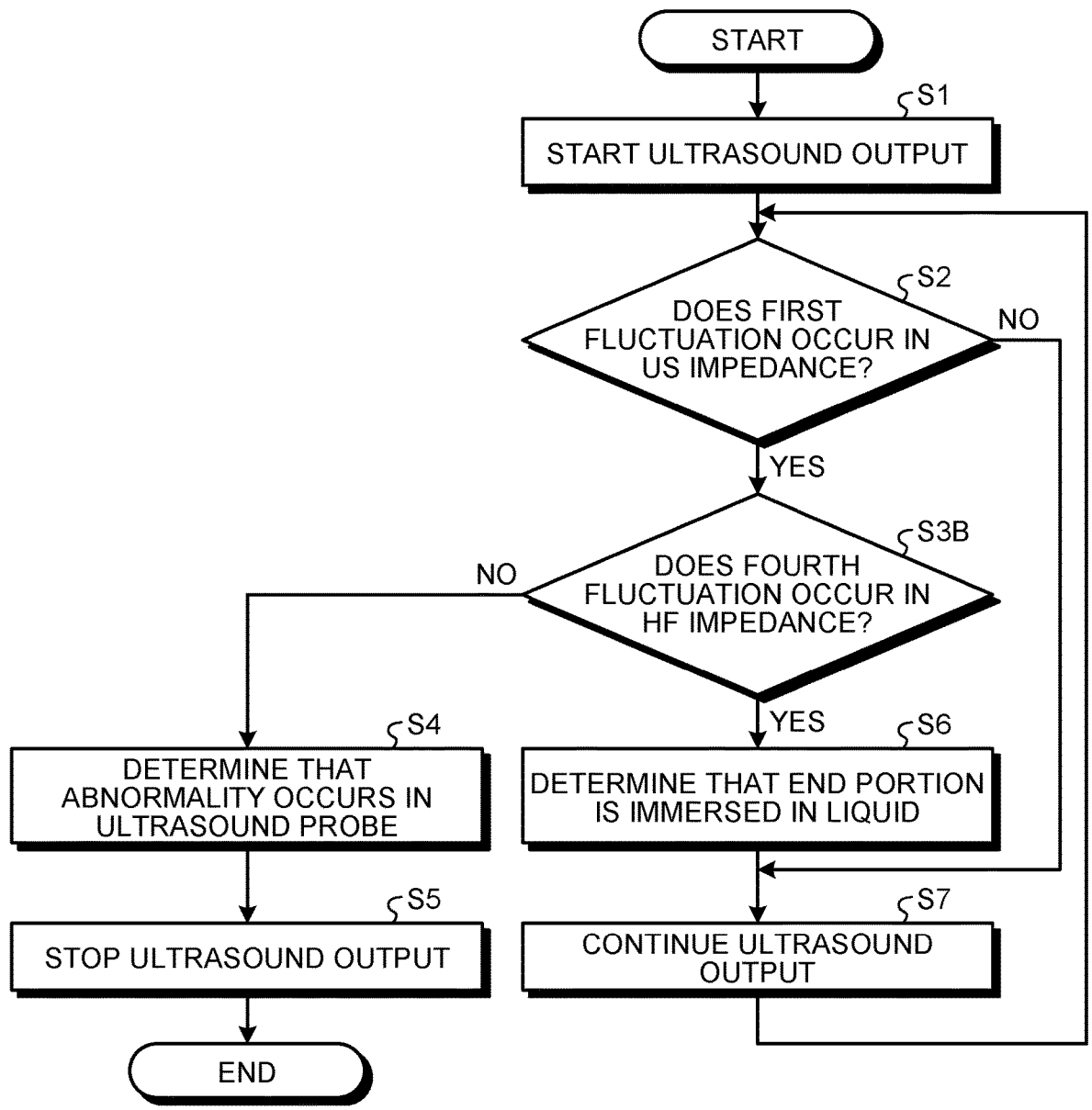
FIG. 8 is a flowchart illustrating a control method according to another exemplary embodiment.

FIG. 8 is a flowchart illustrating a control method according to the third embodiment.

In the above-described first embodiment, the processor 36 determines whether or not the end portion 221 is immersed in the liquid LI (whether or not the cleaning method illustrated in FIG. 4 is being performed) on the basis of fluctuation in the capacitance CA1.

On the other hand, in the third embodiment, the processor 36 determines whether or not the end portion 221 is immersed in the liquid LI on the basis of the fluctuation in the HF impedance Z detected by the HF signal detection circuit 34. Here, the HF impedance Z is derived from $Z=U_1/(I_1-I_{leak})$. $U_1$ corresponds to the HF voltage. The $(I_1-I_{leak})$ corresponds to the HF current.

In the third embodiment, although not specifically illustrated in the drawings, the same configuration (configuration in which the capacitance measurement unit 35 is omitted) as the treatment system 1A (control device 3A) described in the second embodiment described above is adopted.

Hereinafter, the control method according to the third embodiment will be described.

In the control method according to the third embodiment, as illustrated in FIG. 8, Step S3B is adopted instead of Step S3 in the control method described in the first embodiment described above. Therefore, only Step S3B will be described below.

Step S3B is executed in a case where it is determined that the first fluctuation occurs in the US impedance (Step S2: Yes).

Specifically, in Step S3B, the processor 36 monitors the HF impedance Z and determines whether or not a fourth fluctuation occurs in the HF impedance Z.

Meanwhile, as described above, in a case where the HF circuit is in the open state, the leakage current $I_{leak}$ is increased as compared with the closed state or the state immediately before the end portion 221 is immersed in the liquid LI. As a result, the HF impedance Z $(Z=U_1/(I_1-I_{leak}))$ is also increased (HF voltage $U_1$ is constant).

That is, even in a case where the first fluctuation occurs in the US impedance (Step S2: Yes), when the fourth fluctuation occurs in the HF impedance Z (Step S3B: Yes), it can be determined that the first fluctuation in the US impedance is not caused by the occurrence of the abnormality (for example, a crack or the like) in the ultrasound probe 22, but is caused by the immersion of the end portion 221 in the liquid LI. On the other hand, in a case where the first fluctuation occurs in the US impedance (Step S2: Yes) and the fourth fluctuation does not occur in the HF impedance Z (Step S3B: No), it can be determined that the first fluctuation in the US impedance is caused by the occurrence of the abnormality in the ultrasound probe 22.

In a case where it is determined that the fourth fluctuation does not occur in the HF impedance Z (Step S3B: No), the processor 36 causes the processing to proceed to Step S4. On the other hand, in a case where it is determined that the fourth fluctuation occurs in the HF impedance Z (Step S3B: Yes), the processor 36 causes the processing to proceed to Step S6.

Even in a case where it is determined whether or not the end portion 221 is immersed in the liquid LI on the basis of the fluctuation in the HF impedance Z as in the third embodiment described above, the same effects as those of the first embodiment described above are obtained.

Fourth Embodiment

Next, the fourth embodiment will be described.

In the following description, the same reference numerals are given to the same configurations as those of the above-described first embodiment, and the detailed description thereof will be omitted or simplified.

Figure 9:
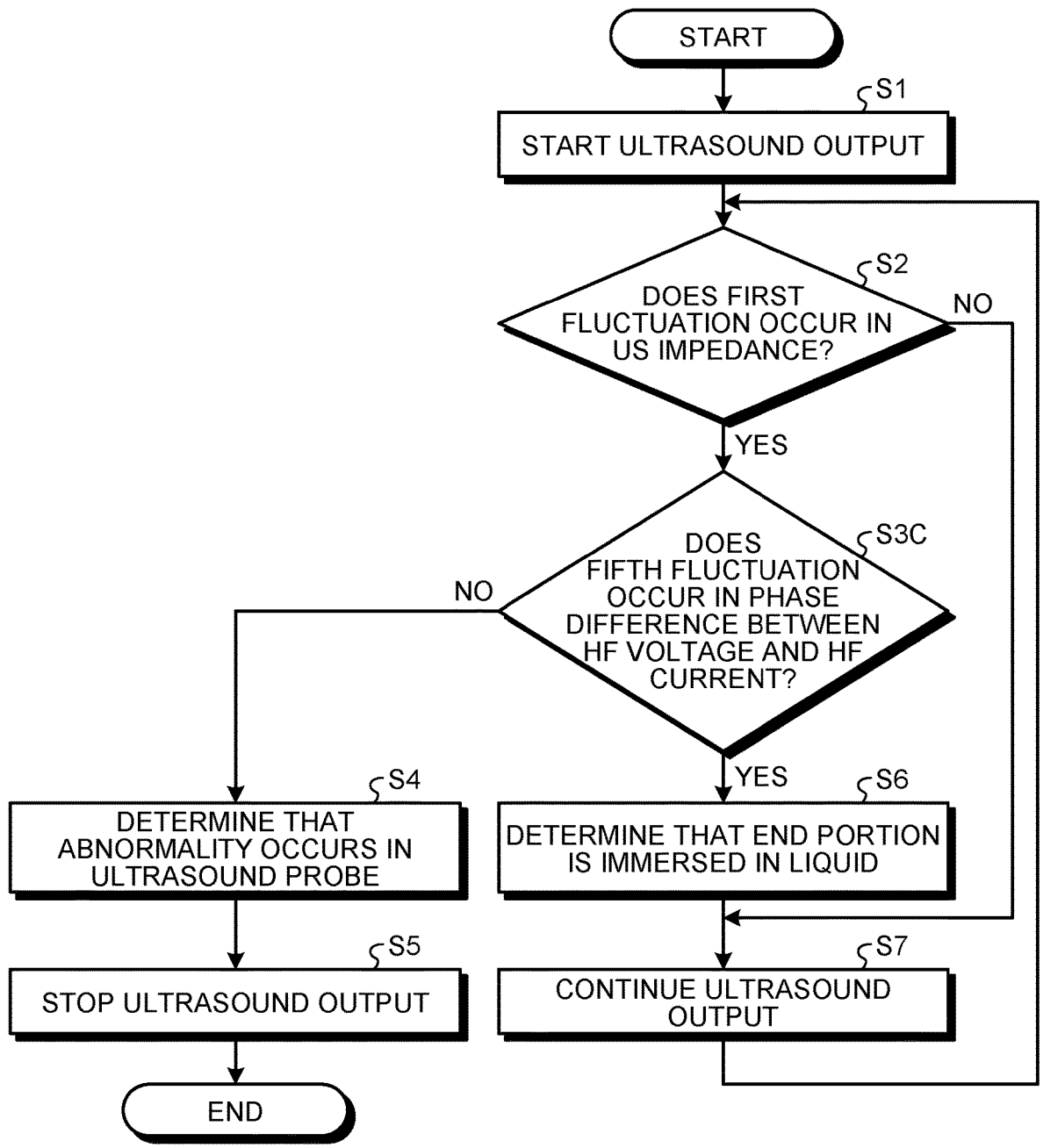
FIG. 9 is a flowchart illustrating a control method according to another exemplary embodiment.

FIG. 9 is a flowchart illustrating a control method according to the fourth embodiment.

In the above-described first embodiment, the processor 36 determines whether or not the end portion 221 is immersed in the liquid LI (whether or not the cleaning method illustrated in FIG. 4 is being performed) on the basis of the fluctuation in the capacitance CA1.

On the other hand, in the fourth embodiment, the processor 36 determines whether or not the end portion 221 is immersed in the liquid LI on the basis of a phase difference between the HF voltage phase signal and the HF current phase signal (phase difference between the HF voltage and the HF current), which are detected by the HF signal detection circuit 34.

In the fourth embodiment, although not specifically illustrated in the drawings, the same configuration (configuration in which the capacitance measurement unit 35 is omitted) as the treatment system 1A (control device 3A) described in the second embodiment described above is adopted.

Hereinafter, the control method according to the fourth embodiment will be described.

In the control method according to the fourth embodiment, as illustrated in FIG. 9, Step S3C is adopted instead of Step S3 in the control method described in the first embodiment described above. Therefore, only Step S3C will be described below.

Step S3C is executed in a case where it is determined that the first fluctuation occurs in the US impedance (Step S2: Yes).

Specifically, the processor 36 calculates the phase difference between the HF voltage phase signal and the HF current phase signal (phase difference between the HF voltage and the HF current), which is detected by the HF signal detection circuit 34. Then, the processor 36 monitors the phase difference between the HF voltage and the HF current, and determines whether or not a fifth fluctuation occurs in the phase difference.

Meanwhile, the liquid LI has a capacitance component (capacitor component). That is, when the end portion 221 is immersed in the liquid LI, the capacitor component of the liquid LI is added to the end portion 221. In an AC circuit, a capacitor advances a phase of a current. Therefore, in a case where the end portion 221 is immersed in the liquid LI, the phase difference between the HF voltage and the HF current changes as compared with a state in which the liquid LI is not immersed.

That is, even in a case where the first fluctuation occurs in the US impedance (Step S2: Yes), when the fifth fluctuation occurs in the phase difference between the HF voltage and the HF current (Step S3C: Yes), it can be determined that the first fluctuation in the US impedance is not caused by the occurrence of the abnormality (for example, a crack or the like) in the ultrasound probe 22, but is caused by the immersion of the end portion 221 in the liquid LI. On the other hand, in a case where the first fluctuation occurs in the US impedance (Step S2: Yes) and the fifth fluctuation does not occur in the phase difference between the HF voltage and the HF current (Step S3C: No), it can be determined that the first fluctuation in the US impedance is caused by the occurrence of the abnormality in the ultrasound probe 22.

In a case where it is determined that the fifth fluctuation does not occur in the phase difference between the HF voltage and the HF current (Step S3C: No), the processor 36 causes the processing to proceed to Step S4. On the other hand, in a case where it is determined that the fifth fluctuation occurs in the phase difference between the HF voltage and the HF current (Step S3C: Yes), the processor 36 causes the processing to proceed to Step S6.

Even in a case where it is determined whether or not the end portion 221 is immersed in the liquid LI on the basis of the fluctuation in the phase difference between the HF voltage and the HF current as in the fourth embodiment described above, the same effects as those of the first embodiment described above are obtained.

Other Embodiments

In the above description, the embodiments for carrying out the disclosure have been described, but the disclosure is not limited only to the above-described first to fourth embodiments.

In the above-described first to fourth embodiments, the ultrasound energy and the high frequency energy can be applied to the target site, but the disclosure is not limited to this.

For example, in the first embodiment, only the ultrasound energy may be applied to the target site. For example, in addition to the ultrasound energy and the high frequency energy, thermal energy may be applied to the target site. Here, "applying thermal energy to a target site" means that heat of a heater or the like is transmitted to the target site.

In the above-described first to fourth embodiments, the treatment tool 2 is configured by a monopolar treatment tool using the return electrode 4, but the disclosure is not limited to this, and the treatment tool 2 may be configured by a bipolar treatment tool in which a pair of gripping members gripping the target site function as a high frequency electrode.

The flow indicating the control method executed by the processor 36 is not limited to an order of processing in the flowcharts (FIGS. 3 and 7 to 9) described in the above-described first to fourth embodiments, and may be changed within a range without contradiction. For example, first to third modification examples illustrated in FIGS. 10 to 12 may be adopted.

Figure 10:
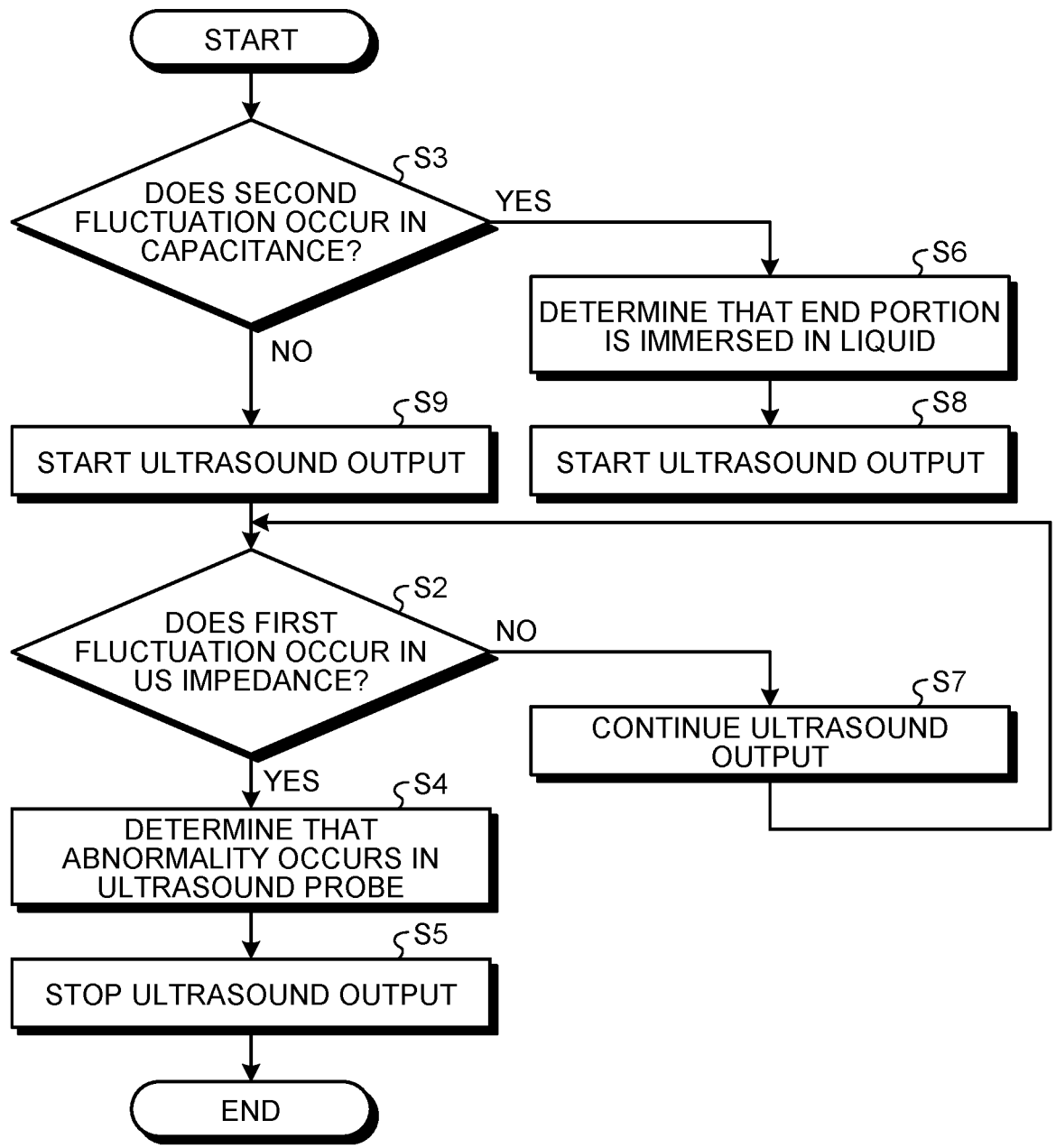
FIG. 10 is a flowchart illustrating another exemplary embodiment.

FIG. 10 is a flowchart illustrating the first modification example of the first to fourth embodiments.

First, the processor 36 executes Step S3 according to the treatment start operation on the switches 211 by the user.

In a case where it is determined that the second fluctuation occurs in the capacitance CA1 (Step S3: Yes), the processor 36 determines that the end portion 221 is immersed in the liquid LI (Step S6), and starts the ultrasound output according to the controlling of the operation of the ultrasound power source 31 (Step S8). Then, the processor 36 continues the ultrasound output until the treatment end operation is performed on the switches 211 by the user.

On the other hand, in a case where it is determined that the second fluctuation does not occur in the capacitance CA1 (Step S3: No), the processor 36 controls the operation of the ultrasound power source 31 and starts the ultrasound output (Step S9).

After Step S9, the processor 36 causes the processing to proceed to Step S2.

In a case where it is determined that the first fluctuation occurs in the US impedance (Step S2: Yes), the processor 36 determines that the abnormality has occurred in the ultrasound probe 22 (Step S4), and stops the operation of the ultrasound power source 31 (stops the ultrasound output) (Step S5). After that, the processor 36 ends this control flow.

On the other hand, in a case where it is determined that the first fluctuation does not occur in the US impedance (Step S2: No), the processor 36 causes the processing to proceed to Step S7. After that, the processor 36 causes the processing to return to Step S2. While Steps S2, and S7 are executed repeatedly, in a case where the treatment end operation is performed on the switches 211 by the user, the processor 36 stops the operation of the ultrasound power source 31 (stops the ultrasound output).

In the first modification example described above, Step S3 is executed before Step S2, and in a case where the second fluctuation occurs in the capacitance CA1 (Step S3: Yes), the ultrasound output is performed without performing the determination in Step S2.

In the first modification example, any one of Steps S3A to S3C may be adopted instead of Step S3.

FIG. 11 is a flowchart illustrating the second modification example of the first to fourth embodiments.

In the second modification example, Steps S3D, S6D, and S7D are added to the first modification example illustrated in FIG. 10. Therefore, only Steps S3D, S6D, and S7D will be described below.

Step S3D is executed in a case where it is determined that the first fluctuation occurs in the US impedance (Step S2: Yes).

Specifically, in Step S3D, the processor 36 determines whether or not the second fluctuation occurs in the capacitance CA1 in a similar manner to Step S3.

In a case where it is determined that the second fluctuation does not occur in the capacitance CA1 (Step S3D: No), the processor 36 causes the processing to proceed to Step S4.

On the other hand, in a case where it is determined that the second fluctuation occurs in the capacitance CA1 (Step S3D: Yes), the processor 36 determines that the end portion 221 is immersed in the liquid LI (Step S6D), and continues the ultrasound output (Step S7D). After that, the processor 36 causes the processing to return to Step S2. While Steps S2, S3D, S6D, and S7D are executed repeatedly, in a case where the treatment end operation is performed on the switches 211 by the user, the processor 36 stops the operation of the ultrasound power source 31 (stops the ultrasound output).

In the second modification example, any one of Steps S3A to S3C may be adopted instead of Steps S3 and S3D.

FIG. 12 is a flowchart illustrating the third modification example of the first to fourth embodiments.

The third modification example is a combination of the first and third embodiments described above.

Specifically, in the third modification example, as illustrated in FIG. 12, the processor 36 causes the processing to proceed to Step S6 in a case where it is determined that the second fluctuation occurs in the capacitance CA1 (Step S3) and it is further determined that the fourth fluctuation occurs in the HF impedance Z (Step S3B). On the other hand, in a case where it is determined to be "No" in Step S3 or Step S3B, the processor 36 causes the processing to proceed to Step S4.

In the third modification example, Step S3 and Step S3B are combined, but the disclosure is not limited to this, and Steps S3 and S3A to S3C may be combined appropriately.

The treatment system and the control device according to the disclosure can improve convenience.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment system comprising:
a treatment tool including an ultrasound transducer configured to generate ultrasound vibration when a drive signal is received, and an end effector configured to apply the ultrasound vibration to a living tissue; and
a control device including an ultrasound power source configured to output the drive signal to the ultrasound transducer, the control device including:
a detection circuit configured to detect a characteristic of the drive signal output from the ultrasound power source; and
a processor configured to control an operation of the ultrasound power source by:
determining whether an abnormality occurs in the end effector, based on at least an output from the detection circuit,
determining whether the end effector is immersed in a cleaning liquid, based on at least the output from the detection circuit, and
continuing an output of the drive signal from the ultrasound power source to the ultrasound transducer when the abnormality occurs in the end effector and the end effector is immersed in the cleaning liquid.

2. The treatment system according to claim 1,
wherein the control device further comprises a capacitance sensor, and the processor is configured to determine whether the end effector is immersed in the cleaning liquid based on a fluctuation in capacitance between the end effector and a ground, based on an output from the capacitance sensor.

3. The treatment system according to claim 1,
wherein the processor is configured to determine whether the end effector is immersed in the cleaning liquid based on a fluctuation in a leakage current between the end effector and a ground, based on a first current value generated by the ultrasound power source and a second current value output from the detection circuit.

4. The treatment system according to claim 1, the control device further comprising a high frequency power source configured to output a high frequency signal to the end effector, wherein:
the end effector is configured to apply high frequency energy based on the high frequency signal, and
the processor is configured to determine whether the end effector is immersed in the cleaning liquid based on a fluctuation in a high frequency impedance, on a voltage value, and a current value in the high frequency signal detected by the detection circuit.

5. The treatment system according to claim 1, the control device further comprising a high frequency power source configured to output a high frequency signal to the end effector, wherein:
the end effector is configured to apply high frequency energy when the end effector receives a high frequency signal, and
the processor is configured to determine whether the end effector is immersed in the cleaning liquid based on a fluctuation in a phase difference between a voltage and a current in the high frequency signal detected by the detection circuit.

6. The treatment system according to claim 1, wherein the processor is configured to:
determine whether a first fluctuation occurs in the end effector based on at least the output from the detection circuit,
determine whether a second fluctuation occurs in the end effector based on at least the output from the detection circuit, and
continue the output of the drive signal from the ultrasound power source to the ultrasound transducer when both the first fluctuation and the second fluctuation occur.

7. The treatment system according to claim 6, wherein the processor is configured to stop the output of the drive signal when the first fluctuation occurs and the second fluctuation does not occur.

8. A control device comprising:
a detection circuit configured to detect a characteristic of a drive signal output from an ultrasound power source configured to output a drive signal to a treatment tool; and
a processor comprising hardware, and configured to control the ultrasound power source by:
determining whether an abnormality occurs in an end effector of the treatment tool, based on at least an output from the detection circuit,
determining whether the end effector is immersed in a cleaning liquid, based on at least the output from the detection circuit, and
continuing the output of the drive signal when the abnormality occurs in the end effector and the end effector is immersed in the cleaning liquid.

9. The control device according to claim 8, wherein the processor is configured to:
determine whether a first fluctuation occurs in the end effector based on at least the output from the detection circuit,
determine whether a second fluctuation occurs in the end effector based on at least the output from the detection circuit, and
continue the output of the drive signal when both the first fluctuation and the second fluctuation occur.

10. The control device according to claim 9, wherein the detection circuit is configured to:
detect an impedance value calculated from a current value and a voltage value in the drive signal, and
output the detected impedance value to the processor.

11. The control device according to claim 10, wherein the processor is configured to:
monitor the detected impedance value output from the detection circuit, and
determine whether the first fluctuation occurs in the detected impedance value.

12. The control device according to claim 9, wherein the processor is configured to stop the output of the drive signal when the first fluctuation occurs and the second fluctuation does not occur.

13. The control device according to claim 9, further comprising a capacitance sensor configured to measure a capacitance between the end effector and a ground,
wherein the processor is configured to determine whether the second fluctuation occurs in the capacitance based on output from the capacitance sensor.

14. The control device according to claim 9, wherein the processor is configured to determine whether the second fluctuation occurs in a leakage current between the end effector and a ground, based on a first current value generated by the ultrasound power source and a second current value output from the detection circuit.

15. The control device according to claim 9, further comprising a high frequency power source configured to output a high frequency signal to the end effector,
wherein the processor is configured to determine whether the second fluctuation occurs in a high frequency impedance calculated from a voltage value and a current value in the high frequency signal.

16. The control device according to claim 9, further comprising a high frequency power source configured to output a high frequency signal to the end effector,
wherein the processor is configured to determine whether the second fluctuation occurs in a phase difference between a voltage and a current in the high frequency signal.

17. The control device according to claim 8, wherein the processor is configured to stop the output of the drive signal when the abnormality occurs in the end effector and the end effector is not immersed in the cleaning liquid.

18. A control method executed by a processor of a treatment system, the method comprising:
determining whether an abnormality occurs in an end effector configured to apply ultrasound vibration to an external medium, the ultrasound vibration being generated by an ultrasound transducer when a drive signal supplied from an ultrasound power source is received, the abnormality being determined based on at least an output from a detection circuit that detects a characteristic of the drive signal output from the ultrasound power source;
determining whether the end effector is immersed in a cleaning liquid, based on at least the output from the detection circuit; and
continuing to output the drive signal from the ultrasound power source to the ultrasound transducer when the abnormality occurs in the end effector and the end effector is immersed in the cleaning liquid.

19. The control method according to claim 18, further comprising:
- determining whether a first fluctuation occurs in the end effector based on at least the output from the detection circuit;
- determining whether a second fluctuation occurs in the end effector based on at least the output from the detection circuit; and
- continuing to output the drive signal from the ultrasound power source to the ultrasound transducer when the first fluctuation and the second fluctuation occur.

20. The control method according to claim 19, further comprising stopping the output of the drive signal when the first fluctuation occurs and the second fluctuation does not occur.

\* \* \* \* \*